United States Patent
Newman et al.

[19]

[11] Patent Number: 5,880,354
[45] Date of Patent: Mar. 9, 1999

[54] GAS SENSOR WITH ORIENTATION INSENSITIVITY

[75] Inventors: Robert L. Newman, Osceola; Patrick B. Blakesley, Goshen, both of Ind.

[73] Assignee: CTS Corporation, Elkhart, Ind.

[21] Appl. No.: 873,219

[22] Filed: Jun. 11, 1997

[51] Int. Cl.[6] .............................. G01N 27/12; H01C 7/10; H01L 7/00
[52] U.S. Cl. .................. 73/25.01; 73/23.32; 73/204.25; 73/23.31
[58] Field of Search .................. 73/25.01, 31.06, 73/23.31, 23.32, 204.19, 204.25

[56] References Cited

U.S. PATENT DOCUMENTS

| | | | |
|---|---|---|---|
| H454 | 4/1988 | Sickenberger et al. | 73/27 R |
| 2,805,134 | 9/1957 | Strange | 23/255 |
| 3,167,947 | 2/1965 | Crawford | 73/23.1 |
| 3,716,337 | 2/1973 | Jones | 23/254 E |
| 3,901,067 | 8/1975 | Boardman, Jr. et al. | 73/23 |
| 4,070,157 | 1/1978 | Iles | 23/254 E |
| 4,222,026 | 9/1980 | Heiney, III et al. | 338/34 |
| 4,298,574 | 11/1981 | Bohl | 422/97 |
| 4,377,944 | 3/1983 | Hishii et al. | 73/23 |
| 4,624,137 | 11/1986 | Johnson et al. | 73/204 |
| 4,674,319 | 6/1987 | Muller et al. | 73/23 |
| 4,696,188 | 9/1987 | Higashi | 73/204 |
| 4,816,800 | 3/1989 | Onaga et al. | 338/34 |
| 4,839,767 | 6/1989 | Yoshioka et al. | 361/42 |
| 4,928,513 | 5/1990 | Sugihara et al. | 73/1 G |
| 4,984,446 | 1/1991 | Yagawara et al. | 73/31.06 |
| 4,991,424 | 2/1991 | Lehto | 73/31.06 |
| 5,012,671 | 5/1991 | Yagawara et al. | 73/31.06 |
| 5,211,053 | 5/1993 | Nolting et al. | 73/31.05 |
| 5,297,419 | 3/1994 | Richardson | 73/25.03 |
| 5,363,091 | 11/1994 | Kotwicki et al. | 340/439 |
| 5,365,216 | 11/1994 | Kotwicki et al. | 340/439 |
| 5,388,443 | 2/1995 | Manaka | 73/31.06 |
| 5,400,643 | 3/1995 | De Angelis et al. | 73/31.06 |
| 5,600,296 | 2/1997 | Kuzuoka et al. | 338/22 R |

*Primary Examiner*—Hezron E. Williams
*Assistant Examiner*—J. David Wiggins
*Attorney, Agent, or Firm*—Michael W. Starkweather

[57] ABSTRACT

A gas sensor for being placed into a gas stream such that the gas sensor is insensitive to any specific rotational orientation about a longitudinal axis of the sensor within the gas stream. The sensor includes 1) a base having an axis that is perpendicular to the gas stream, 2) a sensor element on the base, 3) a catalyzed sensor element on the base proximate the sensor element, for creating an exothermic reaction upon contacting the gas stream thereby forming a heated gas stream portion, and 4) the catalyzed sensor element and the sensor element are positioned on the base with a sufficient axial separation therebetween so that as the base rotates about the axis, the heated gas stream portion will not contact the sensor element. In particular, the base has a second axis being perpendicular to the axis and separating the sensor element from the catalyzed sensor element. Additionally, the invention provides a device that may have both the sensor element and the catalyzed sensor element including a longitudinal axis. Wherein, both the sensor element and the catalyzed sensor element may have many different shapes. Both the sensor element and the catalyzed sensor element may have two or three sides that are coextensive with at least one void. As a result of having a void the base may include a bridge that connects at least one side of the sensor element and the catalyzed sensor element to the base.

27 Claims, 7 Drawing Sheets

GAS SENSOR WITH ORIENTATION INSENSITIVITY

BACKGROUND OF THE INVENTION

CO-PENDING PATENT APPLICATIONS

This application is related to the following:

1) copending U.S. application Ser. No. 08/872,817, entitled, A GAS SENSOR WITH MULTIPLE EXPOSED ACTIVE ELEMENTS, attorney docket no. CTS-1508, filed Jun. 11, 1997, 2) copending U.S. application Ser. No. 08/872,987, entitled A GAS SENSOR WITH MULTI-LEVEL INSENSITIVITY CIRCUITRY, attorney docket no. CTS-1518, filed Jun. 11, 1997, and 3) copending U.S. application Ser. No. 60/017,112, entitled, FUEL SYSTEM LOW CURRENT RHEOSTAT, attorney docket no. CTS-1491, filed May 9, 1996.

The aforementioned are assigned to the assignee named in the present application and are herein incorporated by reference in their entirety.

1. Field of the Invention

This invention relates to a gas sensor, and specifically to a sensor that can rotate about an axis without having a reference sensor element exposed to excess heat generated by a proximate catalyzed sensor element.

2. Description of the Related Art

Various devices are well known for combustible gas detectors used to detect the presence of combustible gases such as those found in car engines. Typical circuits are configured to include at least one sensing element that may be a wire having a catalytic coating. The sensing element was used as one of four legs of a wheatstone bridge circuit. The other three legs consisted of two resistors and a compensator element. The compensator element was identical to the sensing element except that it did not bear a catalytic coating.

A current or voltage was applied to the bridge circuit to heat the surface of the catalytic coating affixed to the sensing element. Since the resistance values of the other three legs of the bridge were known, the resistance in the sensing element could be determined as the current or voltage was passed through the bridge.

When the sensing element was exposed to a combustible gas, such as hydrocarbon, the catalytic coating would begin to burn, increasing the temperature of the sensing element. As the temperature of the sensing element increased, the resistance of the element increased. Accordingly, the current passing through the element decreased. By comparing the resistance level of the sensing element to the resistance level of the compensator element, the presence of a combustible gas could detected. Since the amount of gas present caused a nearly linear increase or decrease in the resistance of the sensing element, the quantity of the gas could be accurately determined by calibrating the change in resistance. This is the basic principal of operation of a catalytic combustible gas sensor. It is noted that often the sensing element must be at a predetermined elevated temperature to properly cause the catalyst reaction with the designated gas.

3. Related Art

Examples of patents related to the present invention are as follows, and each patent is herein incorporated by reference for the supporting teachings:

U.S. patent statutory registration no. H454, is a chemical agent leak detector and a method of using the same.

U.S. Pat. No. 5,400,643, is a gas sensor based on semi-conductor oxide, for gaseous hydrocarbon determination.

U.S. Pat. No. 5,388,443, is an atmosphere sensor and method for manufacturing the sensor.

U.S. Pat. No. 5,365,216, is a catalyst monitoring device using EGO sensors.

U.S. Pat. No. 5,363,091, is a catalyst monitoring device using EGO sensors.

U.S. Pat. No. 5,211,053, is a hot gas sensor device with improved thermal isolation from carrier plate.

U.S. Pat. No. 5,012,671, is a gas detecting device.

U.S. Pat. No. 4,991,424, is an integrated circuit heatable sensor.

U.S. Pat. No. 4,984,446, is a gas detecting device and gas detecting system using the same.

U.S. Pat. No. 4,928,513, is a sensor.

U.S. Pat. No. 4,839,767, is an element and device for detecting internal faults in an insulating gas charged electrical apparatus.

U.S. Pat. No. 4,816,800, is an exhaust gas sensor.

U.S. Pat. No. 4,674,319, is an integrated circuit sensor.

U.S. Pat. No. 4,377,944, is an integrated gas sensitive unit comprising a gas sensitive semiconductor element and a resistor for gas concentration measurement.

U.S. Pat. No. 3,901,067, is a semiconductor gas detector.

The foregoing patents reflect the state of the art of which the applicant is aware and are tendered with the view toward discharging applicants' acknowledged duty of candor in disclosing information that may be pertinent in the examination of this application. It is respectfully stipulated, however, that none of these patents teach or render obvious, singly or when considered in combination, applicant's claimed invention.

4. A Related Problem

Referring to FIG. 1, there is a previous design from the present inventors that illustrates one problem to be overcome by the additionally now disclosed preferred embodiments. Specifically, there is a sensor 10 having a base 12 with signal conditioning circuitry 14 that receives signals via traces 24 and 26 from sensing element structures 17 and 19, which are located on either side of longitudinal axis 11. Uniquely, the sensing element structures 17 and 19 are made up of sensing elements 20 and 21 that are located on parallel bridges 22 and thermally isolated by voids 18. In operation, one skilled in the art will realize that all of the electrical signals will be skewed if the heated air flow 27 first interacts with the catalyzed sensing element and then contacts the reference sensor. The air contacting the reference sensor will have been heated by the catalytic reaction, thus skewing any resulting signals. To avoid this problem, great care must be given to ensure that the air 27 does not contact the sensor elements in this fashion. In particular, the sensor would have to be placed so the air either hits both sensors simultaneously or hits the reference sensor first. In either case it is very difficult to make sure that the sensor is so arranged when placing it in an exhaust gas air stream. However, the present invention has overcome the need for careful placement of the sensor 10 in air stream 27 and thus eliminating the potential signal skewing problem.

This and other problems will be solved by the preferred embodiments of the invention. A review of the specification, drawings, and claims will more clearly teach a skilled artisan of other problems that are solved by the preferred embodiments.

SUMMARY OF THE INVENTION

It is a feature of the invention to provide a gas sensor for being placed into a gas stream. The sensor includes 1) a base having an axis, 2) a sensor element on the base, 3) a catalyzed sensor element on the base proximate the sensor element to have a similar temperature to the sensor element, for creating an exothermic reaction upon contacting the gas stream thereby forming a heated gas stream portion, and 4) the catalyzed sensor element and the sensor element are positioned on the base so that as the base rotates about the axis, the heated gas stream portion will not contact the sensor element.

A further feature of the invention includes the base having a second axis being perpendicular to the axis and separating the sensor element from the catalyzed sensor element.

Still a further feature of the invention may include having the catalyzed sensor being a mirror image of the sensor element.

An additional feature of the invention may be a device that has both the sensor element and the catalyzed sensor element with a longitudinal axis. Wherein both of the sensor elements may have parallel longitudinal axis. Wherein both of the sensor elements may be parallel to the axis of the base. Wherein both of the sensor elements may have co-extensive longitudinal axes.

A further feature of the invention may be that both the of sensor elements to be arcuate in shape.

Yet, an additional feature is that both the sensor element and the catalyzed sensor element may be at an angle to the axis.

Still a further feature of the invention is that the base has at least one void therein. Wherein both the sensor elements may have two or three sides that are coextensive with at least one void.

A further feature of the invention is that the base may include a bridge that connects at least one side of the sensor element and the catalyzed sensor element to the base.

A further feature of the invention is to provide a device that has a ceramic substrate and a glass layer for adhering a catalyst support layer to the substrate. The catalyst support structure is comprised of high surface area ceramic particles. A catalytic material is deposited on the catalytic support structure for reacting with the gas to be sensed.

The invention resides not in any one of these features per se, but rather in the particular combination of all of them herein disclosed and claimed. Those skilled in the art will appreciate that the conception, upon which this disclosure is based, may readily be utilized as a basis for the designing of other structures, methods and systems for carrying out the several purposes of the present invention. Further, the abstract is neither intended to define the invention of the application, which is measured by the claims, neither is it intended to be limiting as to the scope of the invention in any way.

Figure 1:
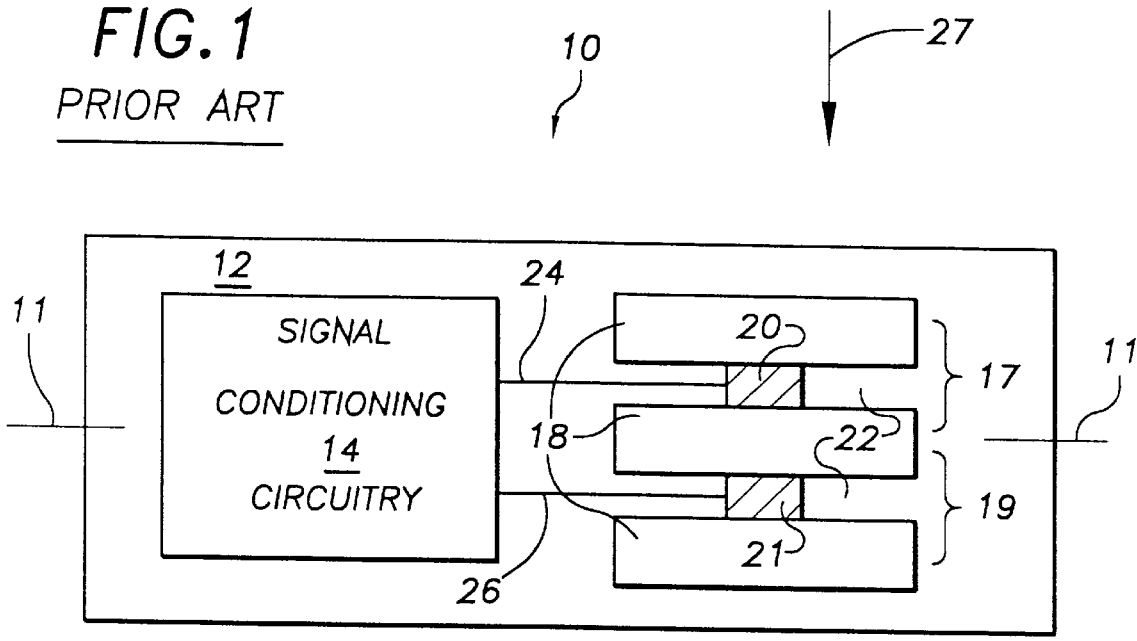
FIG. 1 is one embodiment of a gas sensor designed by the inventors that illustrates one problem overcome by the preferred embodiments.

It is noted that the drawings of the invention are not to scale. The drawings are merely schematic representations, not intended to portray specific parameters of the invention. The drawings are intended to depict only typical embodiments of the invention, and therefore should not be considered as limiting the scope of the invention. In the drawings like numbering represents like elements between the drawings.

DETAILED DESCRIPTION OF THE PREFERRED EMBODIMENT

Figure 2:
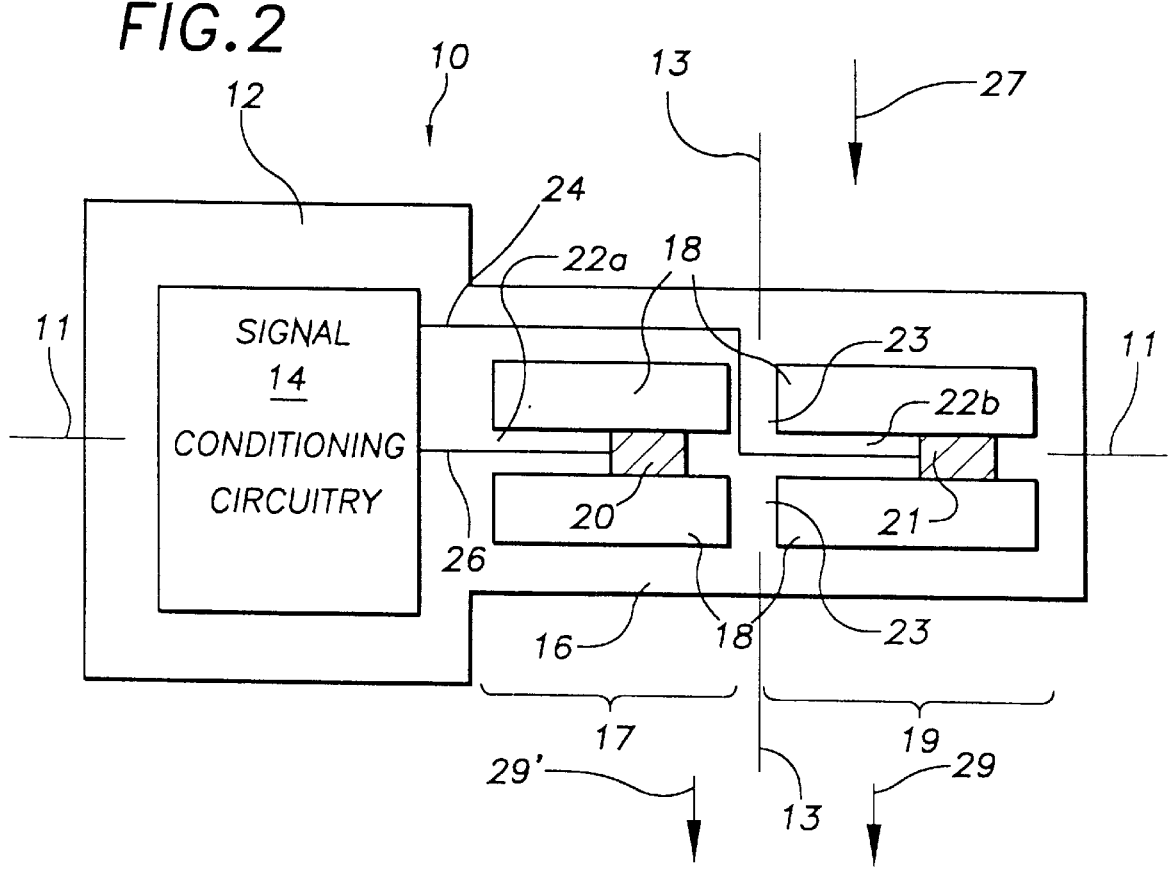
FIG. 2 is one embodiment of the invention.

The present invention provides a gas sensor for determining gas concentrations in an air stream. Referring to FIG. 2, there is a preferred embodiment of the gas sensor 10. Specifically, the gas sensor 10 has a base 12, which has a longitudinal axis 11 that is oriented to be at an angle to the gas stream 27, illustrated as being perpendicular. There is also a reference sensor element 20 on base 12, and a catalyzed sensor element 21 proximate the reference sensor element 20. As known in the art, the catalyzed sensor element 21 creates an exothermic reaction upon contacting the gas stream thereby forming a heated gas stream portion 29. The gas stream flowing past the sensor element 20 would not create a heated gas stream portion 29'. The base also has an extension portion 16, located between the signal conditioning circuitry 14 and the sensor regions 17, 19, for creating a distance between the circuitry 14 and the heated sensor regions 17, 19. Although extension portion 16 is illustrated as being relatively short, in reality it could be relatively long to protect the circuitry 14 from the detrimental high temperatures associated with the operational temperature ranges of the sensor elements 20, 21. The sensor regions 17,19 could be operating, for example, from 200 to 500 plus degrees Celsius for proper operation. However, the conditioning circuitry 14 would need to be operated around a maximum of 150 degrees Celsius for optimum signal processing. Thus, by regulating the length of extension section 16, it is possible to keep the signal conditioning circuitry 14 in a proper operational temperature range.

In the present embodiment, both sensor elements 20, 21 are located upon two separate bridge sections 22a, 22b. Additionally, these bridge sections are isolated from any heat sink effects from the base 12 by voids 18 located on at least either side of the bridges. In this arrangement, it is possible to have both sensor elements 20, 21 closer in temperature so that any change in electrical resistance would not be due to ambient gas stream heat. Thus, only exothermic heat from the catalytic reaction on the measuring sensor element will cause a notable difference between the two resistances of the two sensor elements. It is advantageous to have both sensor elements to be close in temperature to avoid having compensating circuitry and other means for adjusting for the temperature differences. With various designs of the bridges, voids, and sensor elements, it is possible to have temperature differences below 80 degrees Celsius and optimumly below 50 degrees Celsius when operating in 200 to 600 or more degrees Celsius. It is noted that the ideal situation would be to have no difference in temperature between the sensor elements except for the exothermic catalytic reaction effects.

Of particular note, horizontal axis 13 separates sensor regions 17 and 19. It is this separation that provides for the advantage of orientation insensitivity. Specifically, the sensor 10 may rotate about axis 11 and in no position will the heated gas stream portion 29 affect the reference non-catalyzed sensor 20. This is a great advantage over the previous design considered by the inventors in FIG. 1, where the sensor is very orientation sensitive for proper operation. Of course, this situation only works if the gas stream is substantially perpendicular to the longitudinal axis 11. Also keep in mind that the gas stream most likely will already be heated but a skilled artisan will realize that the catalytic reaction with the gas will further heat the gas stream, thus creating the "extra" or catalyticly heated gas stream portion 29.

Figure 3:
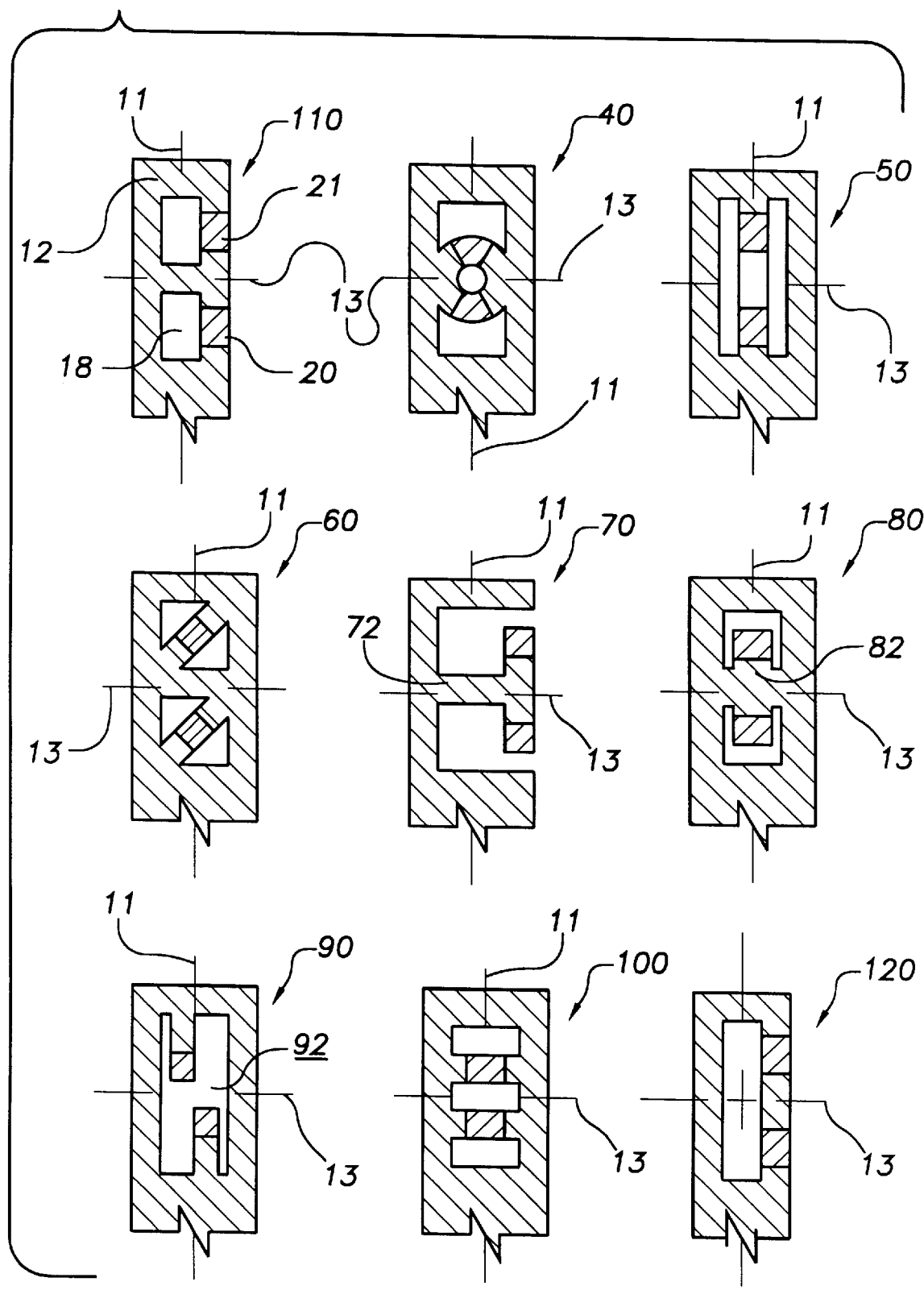
FIG. 3 illustrates several other design embodiments of the invention.

Referring to FIG. 3 there is illustrated several potential designs for the sensor. In particular, sensors 40, 50, 60, 70, 80, 90, 100, 110, and 120 all have a substrate 12, a sensor element 20 and a catalyzed sensor element 21, a longitudinal axis 11, a horizontal axis 13, and some type of void that thermally isolates the sensor elements from the base.

There are several distinguishing features to separate the various types of sensor configurations. There are the single bridge sensors, typically sensor 70 and 80 incorporate a single bridge 72 or 82 respectively that connects the two sensor elements 20, 21 to the main body of the base 12 via a single bridge. There are the single bridge sensors 40, 50, 110, and 120, which have both sensor elements on a single bridge but allow for electrical connection of the sensor elements to the main body of the base along two or more paths. There are the two bridge sensors 60, 90, and 100, which have the two sensor elements located on two separate bridges that are basically separate from each other. There are the axially balanced sensors 40, 50, 60, 80, and 100, which have an equal amount of sensor element mass located on either side of the longitudinal axis 11. There is the offsetting sensor design 90, that has the sensor element on one side of the longitudinal axis 11 and opposite to the other sensor element. There is the asymmetrical sensors 70, 110, and 120, which have both sensors located on one side of the longitudinal axis 11. All of the sensor designs are horizontally balanced sensors, where each sensor element is located on opposite sides of the horizontal axis 13.

Figure 4:
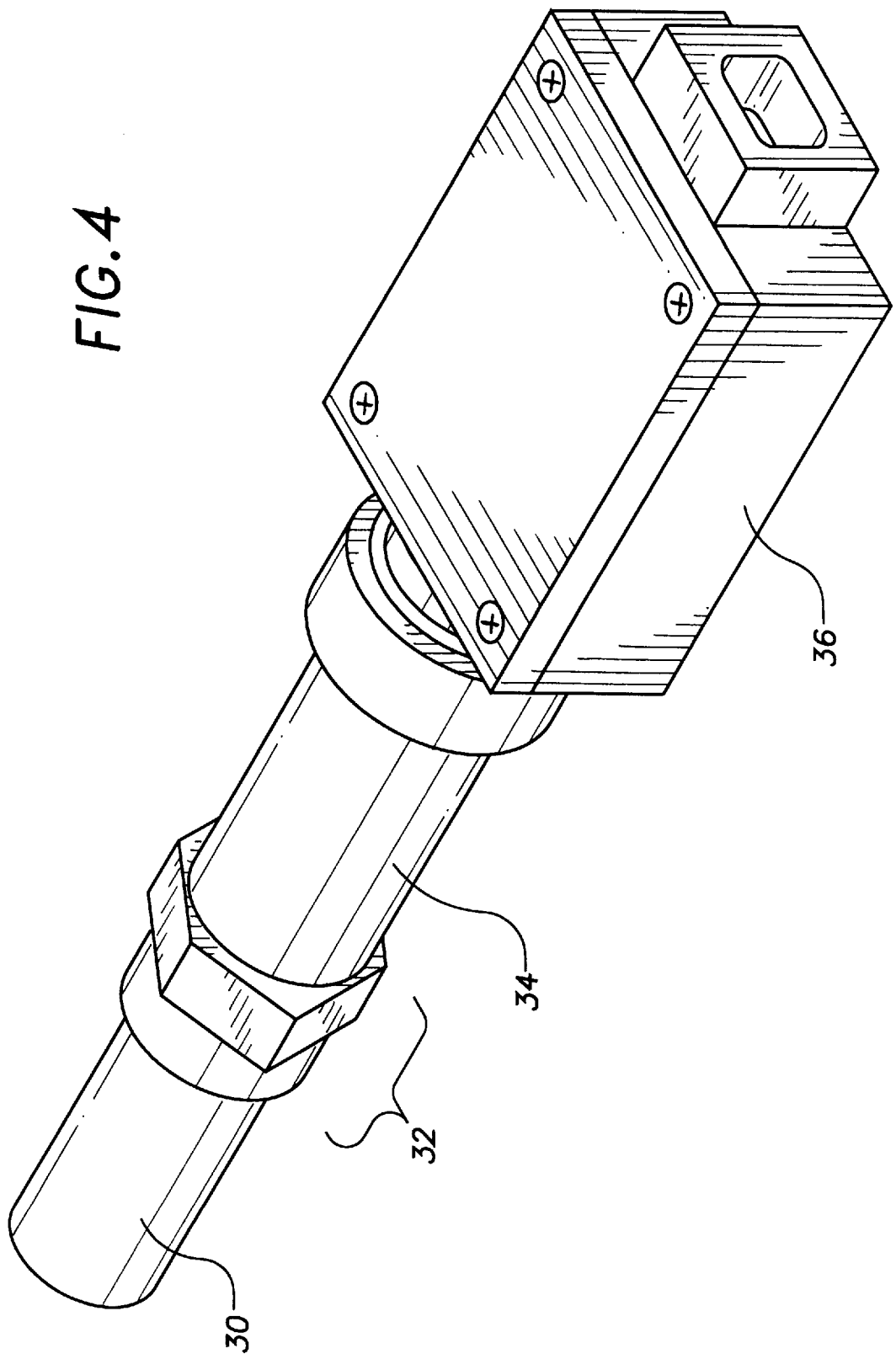
FIG. 4 illustrates a housing for holding the sensor.

Referring to FIG. 4, there is illustrated a housing for holding the sensor 10. In particular there is a hollow air pervious porous cap 30 for encapsulating the sensing elements 20, 21. There is also an attachment 32 for coupling the cap 30 to a spacer 34. The spacer serves the purpose of extending the electronics housing 36 far enough away from the cap 30, since the cap region is the hottest area and the housing holds the conditioning circuitry 14, which requires lower temperatures for proper operation. The electronics housing 36 protects the conditioning circuitry 14 and provides support for coupling the sensor to output wires to communicate with remote analysis circuitry (not shown). The whole assembly is mounted onto an exhaust pipe just after a catalytic converter. Of course only the porous cap 30 should be located in the exhaust pipe to remove the electronics from the hot temperatures.

Figure 5:
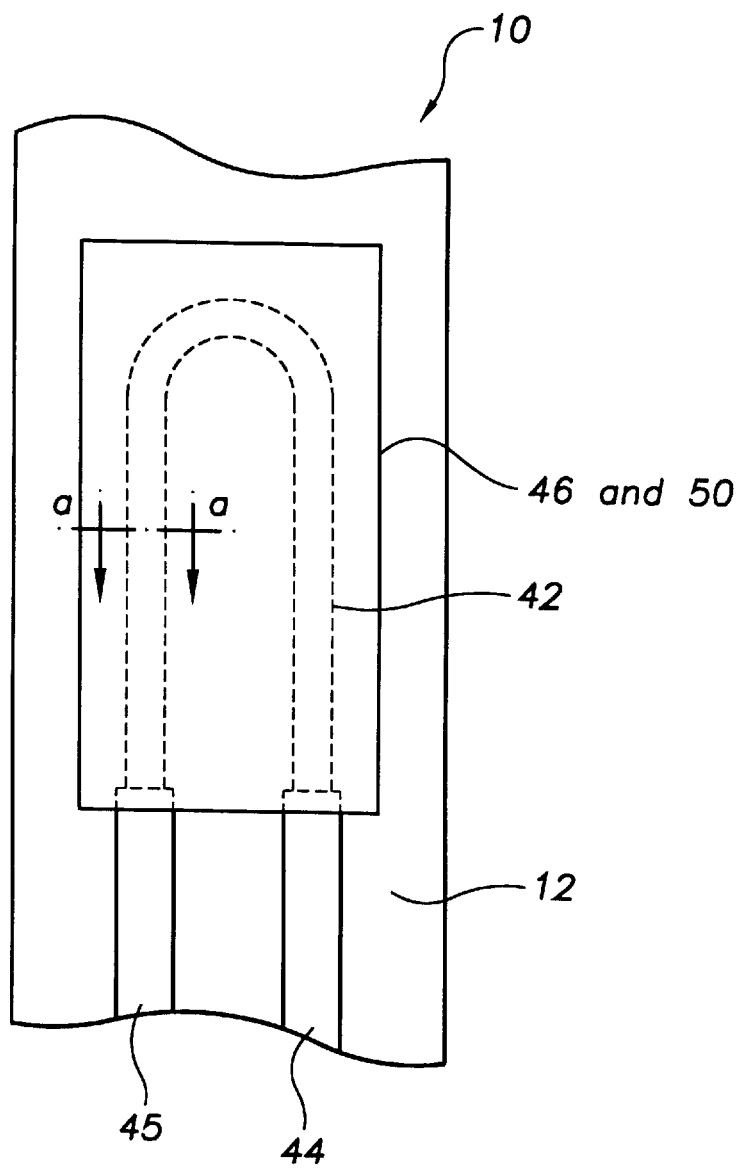
FIG. 5 is a plan view showing a closeup of the sensor element region.

The present invention provides a gas sensor having a multilayered structure. The structure is ideally suited to sensing hydrocarbons and nitrogen oxides in an automobile exhaust system. Regarding FIG. 5, there is a plan view of the gas sensor 10 showing a portion of a substrate (base) 12. Substrate 12 is preferably made out of a ceramic material but other suitable dielectric materials may be utilized. Only the portion of substrate 12 containing a catalytic support structure 50 and glass adhesion layer 46 has been included in FIG. 5.

The remaining portion of substrate 12 can take on any desired configuration that will supply the necessary structural and thermal properties for the sensor. For instance, the structure must be strong enough to survive the shock and vibration attendant in an automobile exhaust system. In addition, the thermal properties must be such that any catalytic reactions occurring on catalytic support structure 50 can be detected by a thermally sensitive resistor element 42 located on substrate 12 (i.e. the substrate must not extract so much heat from the catalytic reaction that there is no resulting temperature increase in resistor element 42).

Located on substrate 12 and electrically connected to resistor element 42, are conductors 44 and 45. Conductors 44 and 45 are connected to circuitry (not shown) that can detect resistance changes from accompanying voltage drops along the length of resistor element 42.

Figure 6:
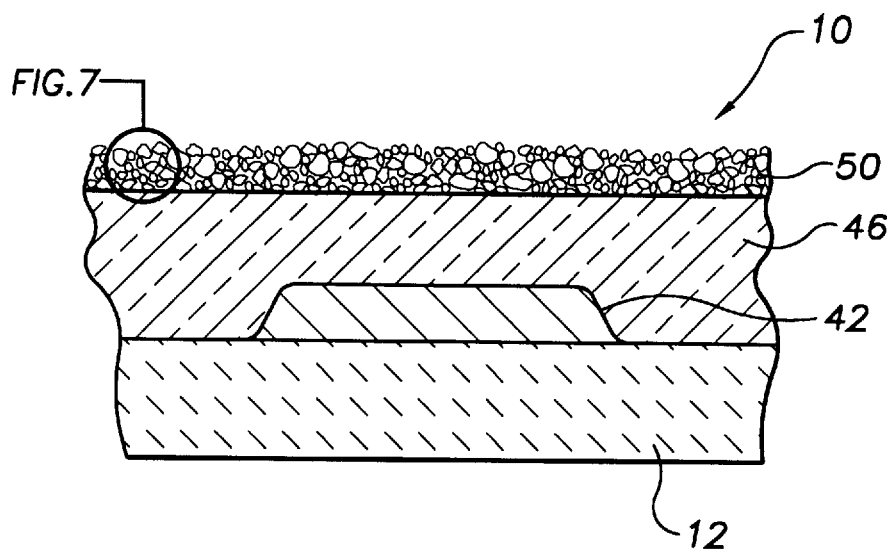
FIG. 6 is a cross-section of FIG. 5 taken through section a—a showing one embodiment for a multilayered structure.

In FIG. 6, a cross section taken through resistor element 42 is depicted. Resistor element 42 can be deposited on substrate 12 using any conventional thick or thin film technique as long as the deposit is robust enough to withstand the environment of an auto exhaust system and the thermal coefficient of resistivity is high enough so that the resistor will respond to temperature changes from catalytic reactions. The material used to form resistor element 42 can be selected using these same criteria. In the preferred embodiment, it was found that platinum is a suitable material for resistor element 42 and that screen printing proved to be a suitable deposition method.

Conductors 44 and 45 can likewise be deposited using any conventional thick or thin film technique. Gold was selected as the conductor material for the preferred embodiment.

A layer of glass 46 is deposited over the resistor element 42. One way of forming glass layer 46 is to mix powdered glass with an organic solvent and screen print the mixture on the substrate. The glass layer can also be formed using a doctor blade or brushing the mixture on. The layer of glass 46 is then dried but not fired yet. This provides a firm surface on which to deposit the catalytic support structure 50, but still enables the glass to act as an adhesion promoter when the structure is subsequently fired.

The catalytic support structure 50 is comprised of high surface area particles such as powdered alumina. The particles can be calcined before applying them to the sensor structure to help assure that they have a high surface area for receiving a catalyst coating. The alumina particles can be combined with aluminum hydroxide or a similar substance to form a paste for application. The paste can be applied with thick film techniques such as screen printing.

After catalytic support structure 50 is applied the entire assembly is fired at the proper firing profile for the glass employed. This will reflow the glass and cause it to firmly adhere to both the alumina particles and substrate 12. It is important that the glass bond very firmly to both the substrate and catalytic support because if the alumina particles flake off, the sensor will no longer function. In principal, any glass film formation, including many commercially available varieties such as GA-4 from Nippon Electric Glass, can be used as described above, provided it has the property of adhering to both substrate 12 and the catalytic support structure 50. A temperature of 700 degrees centigrade for 1 hour is sufficient to reflow the GA-4 glass.

The final step is to apply a catalyst to catalytic support structure 50. In the preferred embodiment for a hydrocarbon sensor, platinum is used for the catalyst. The platinum is applied as a chloroplatinic acid solution using a dropper or other suitable technique. Afterwards the entire structure is again fired at about 500 degrees centigrade for 1 hour to reduce the acid to platinum.

Figure 7:
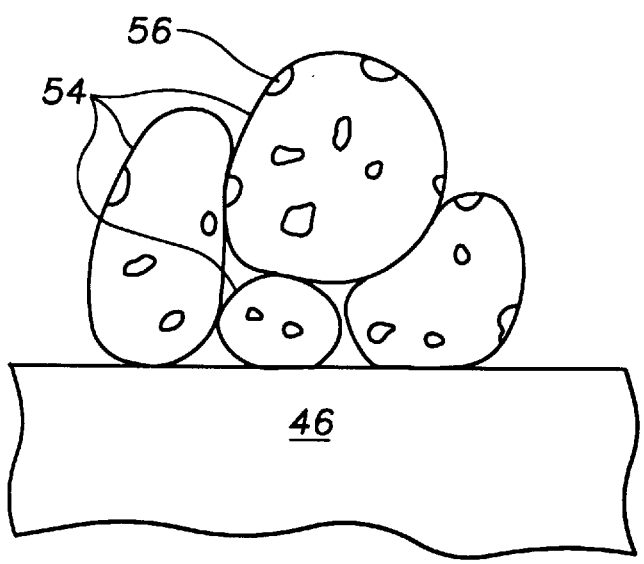
FIG. 7 is an enlargement of a portion of FIG. 6 showing the catalyst support structure.

The final catalytic support structure, as shown by the enlarged view in FIG. 7, is comprised of alumina particles 54 adhered to glass layer 46. The particles vary in size and shape and the surface may include pores 56. When the chloroplatinic acid is applied and dried as described above, the surfaces of particles 54, including the surfaces of pores 56, will be covered by a very fine layer of platinum.

Figure 8:
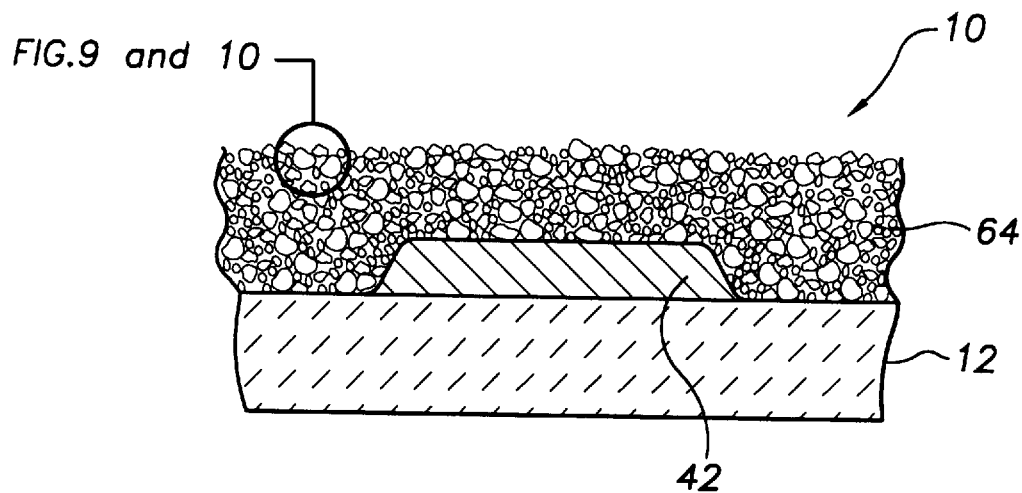
FIG. 8 is a cross-section of FIG. 5 taken through section a—a showing another embodiment for a compounded catalytic structure before firing.

In FIG. 8, a cross section taken through resistor element 42 is depicted. Resistor element 42 can be deposited on substrate 12 using any conventional thick or thin film technique as long as the deposit is robust enough to withstand the environment of an auto exhaust system and the thermal coefficient of resistivity is high enough so that the resistor will respond to temperature changes from catalytic reactions on the overlaid support structure. The material used to form resistor element 42 can be selected using these same criteria. In the preferred embodiment, it was found that platinum was a satisfactory material for resistor element 42 and that screen printing proved to be a suitable deposition method.

Figure 9:
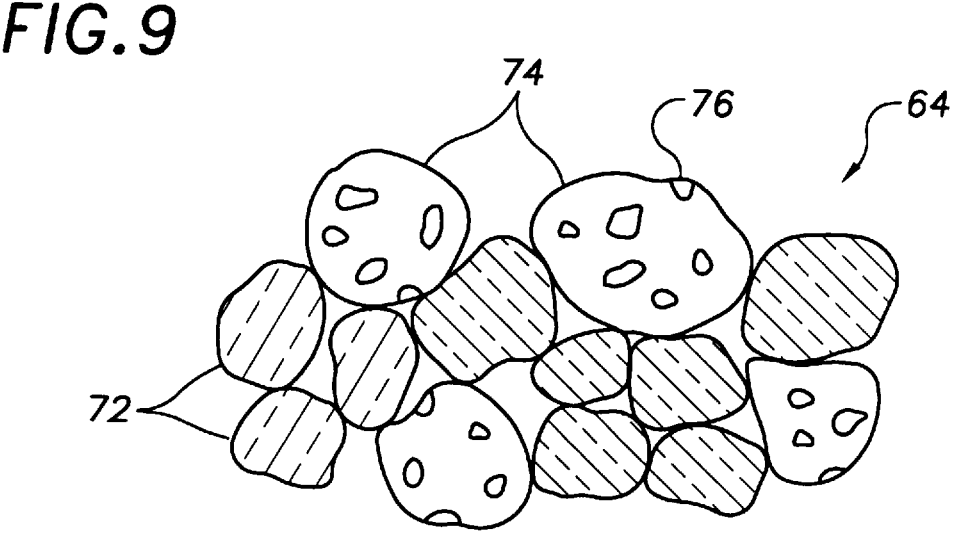
FIG. 9 is an enlargement of the circled portion of FIG. 8 showing greater detail of the catalyst support structure.
Figure 10:
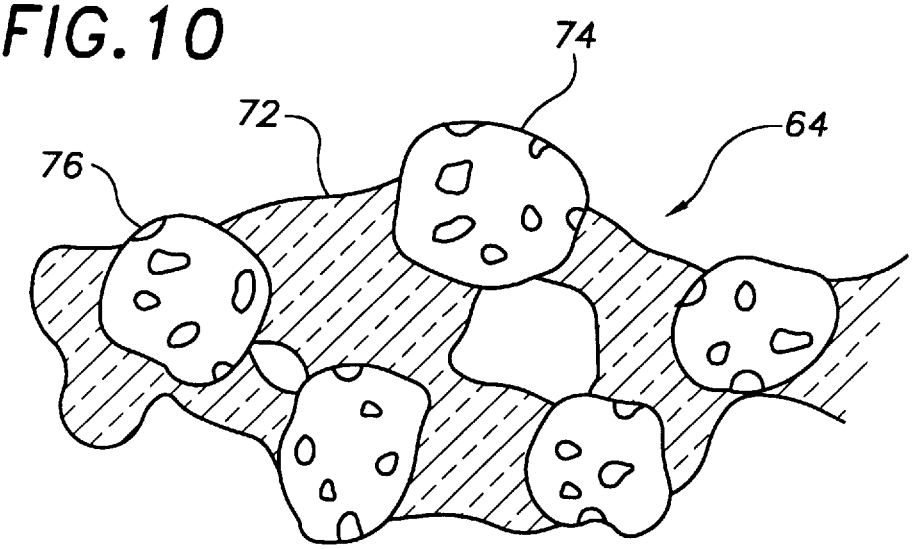
FIG. 10 shows what the structure of FIG. 9 looks like after it has been fired, and the glass has been reflowed.

As shown in FIG. 9 and 10, the catalyst support structure 64, comprises a mixture of alumina particles 74 and powdered glass 72. In the preferred embodiment, the mixture includes 20% LaRoche V700 alumina and 80% GA-4 glass from Nippon Electric Glass. The alumina is calcined at about 600 degrees Centigrade for 1 hour before it is added to the mixture. This helps assure that the alumina will have a high surface area for a catalyst coating. Sufficient screening agent is added to the mixture to obtain a paste like consistency. The screening agent used in the preferred embodiment is comprised of an organic solvent, a rheology modifying solid and a wetting agent.

The mixture is deposited over the resistor element 42. Screen printing is one suitable method of depositing the mixture; although it can also be deposited using a doctor blade, brushing etc. After catalytic support structure 64 is applied, the entire assembly is heated at a temperature that will reflow the glass employed. A temperature of 700 degrees centigrade for 1 hour is sufficient to reflow the GA-4 glass 72, and cause it to firmly adhere to both the alumina particles 74 and substrate 12 as shown in FIG. 10. It is important that the glass bond very firmly to both the substrate and catalytic support because if the alumina particles flake off, the sensor will no longer function.

The final step is to apply a catalyst to catalytic support structure 64. In the preferred embodiment for a hydrocarbon sensor, platinum is used for the catalyst. The platinum is applied as a chloroplatinic acid solution using a dropper or other suitable technique. Afterwards the entire structure is reheated at a temperature that is high enough to reduce the acid to platinum. A temperature of 500 degrees centigrade was used for the preferred embodiment.

Alumina particles 74 vary in size and shape and the surface may include pores 76. When the chloroplatinic acid is applied and dried as described above, the surfaces of particles 74, including the surfaces of pores 76, will be covered by a very fine layer of platinum. Of course, some platinum will also adhere to the surfaces of glass 72.

Operation of the Sensor

The key to the operation of the sensor is the catalytic reaction of the gas to be sensed and the ability of the resistor element to respond to this reaction by a resulting change in its resistance. For example, as a hydrocarbon gas contacts the platinum catalyst, a chemical reaction occurs in which the hydrocarbon is combusted and heat is generated. The greater the quantity of hydrocarbons, the more heat is produced, thus causing the resistance of resistor element 42 to rise accordingly. The resistance of resistor element 42 is then compared to the resistance of a reference sensor (not shown), which is in the same environment and of the same design, except that it is not covered with a catalyst. The difference in the resistance between resistor element 42 and the reference sensor (not shown) is due to the heat generated by the catalytic reaction. The resistance difference indicates the concentration of hydrocarbons in an exhaust stream.

Variations of the Preferred Embodiment

Although the illustrated embodiments discuss the arrangement of the sensor and signal conditioning circuitry 14 to be on a single base, one skilled in the art will realize that the preferred embodiment would work with most any arrangement. For example, the signal conditioning circuitry 14 could be on a separate base, where the sensor element containing base is, for example, solder connected to the signal conditioning circuit containing base. Additionally, the second base containing the conditioning circuitry could also be a printed circuit board and not ceramic material like the sensor element base.

Although, only nine designs for the sensor were illustrated in FIG. 3, one skilled in the art would be able to envision many variations. Additionally, even though the preferred embodiment discusses a horizontal and longitudinal axis, a skilled artisan would not be constrained by the descriptive wording of horizontal and longitudinal. In fact, the sensor may not even have an axis that is longer than the other, it could even be shorter, in which case the word longitudinal would be inaccurate. Of course, a skilled artisan would be able to use the preferred embodiment to detect numerous types of gases by using various catalysts and heating methods.

Although the preferred embodiment discusses the location of the catalyzed sensor to be closest to the far end of the sensor, i.e. sensor 21, it is equally workable to have the catalyzed sensor to be located furthest away from the top of the sensor base, i.e. sensor 20 location. Thus, a reversal of the positions is often needed dependent upon the orientation of the overall gas sensor in the gas stream. In these variations, it is still possible to have the heated gas stream portion 29 not contact the reference sensor 20 or 21 dependent upon the orientation design.

A further variation of the preferred embodiment is to have the longitudinal axis at most any angle to the gas stream that would allow rotation about the axis that would not have the catalyzed heated gas stream portion contact the reference sensor. This arrangement works especially well if the whole sensor were inserted into the gas stream at a right angle. However, for example, the sensor housing could be at an acute angle oriented any way in the gas stream. If oriented toward the gas stream, of course the catalyzed sensor would be located below the non-catalyzed sensor (i.e. further away from the one end of the base). In this arrangement, the sensor base 12 could be rotated about the longitudinal axis without having the heated gas stream potion contacting the reference sensor elements.

While the invention has been taught with specific reference to these embodiments, someone skilled in the art will recognize that changes can be made in form and detail without departing from the spirit and the scope of the invention. The described embodiments are to be considered in all respects only as illustrative and not restrictive. The scope of the invention is, therefore, indicated by the appended claims rather than by the description. All changes that come within the meaning and range of equivalency of the claims are to be embraced within their scope.

What is claimed and desired to be secured by Letters Patent is:

1. A gas sensor for being placed into a gas stream and designed to be insensitive to a specific rotational orientation while performing measurements on the gas stream, comprising:
   a) a base having an axis that is at an angle to the gas stream;
   b) a sensor element positioned on the base, for sensing a first temperature at a first point along the gas stream;
   c) a catalyzed sensor element, positioned on the base, for both creating an exothermic reaction upon contacting the gas stream thereby forming a heated gas stream portion having a second temperature equal to or hotter than the first temperature, and sensing the second temperature at a second point along the gas stream proximate the first point; and
   d) the catalyzed sensor element and the sensor element are positioned on the base with a sufficient separation along the axis therebetween so that as the base would rotate about the axis the heated gas stream portion created by the catalyzed sensor element would not contact the sensor element.

2. The gas sensor of claim 1, wherein the base includes a second axis being perpendicular to the axis and separating the sensor element from the catalyzed sensor element.

3. The gas sensor of claim 2, wherein the catalyzed sensor element shape is a mirror image of the sensor element shape.

4. The gas sensor of claim 3, wherein both the sensor element and the catalyzed sensor element have a longitudinal axis.

5. The gas sensor of claim 4, wherein both the sensor element and the catalyzed sensor element have a parallel longitudinal axis.

6. The gas sensor of claim 5, wherein both the sensor element and the catalyzed sensor element are parallel to the axis of the base.

7. The gas sensor of claim 5, wherein both the sensor element and the catalyzed sensor element have co-extensive longitudinal axes.

8. The gas sensor of claim 2, wherein both the sensor element and the catalyzed sensor element are arcuate in shape.

9. The gas sensor of claim 2, wherein both the sensor element and the catalyzed sensor element are at an angle to the axis.

10. The gas sensor of claim 1, wherein the base has at least one void therein.

11. The gas sensor of claim 10, wherein both the sensor element and the catalyzed sensor element have two sides that are coextensive with at least one void.

12. The gas sensor of claim 11, wherein both the sensor element and the catalyzed sensor element have three sides that are coextensive with at least one void.

13. The gas sensor of claim 11, wherein the base includes a bridge that connects at least one side of the sensor element and the catalyzed sensor element to the base.

14. The gas sensor of claim 12, wherein the base includes a bridge that connects at least one side of the sensor element and the catalyzed sensor element to the base.

15. The gas sensor of claim 1, further includes signal conditioning circuitry, for conditioning signal from the catalyzed sensor element and the sensor element.

16. The gas sensor of claim 15, wherein the base includes an extension portion for separating the conditioning circuitry from the catalyzed sensor element and the sensor element.

17. The gas sensor of claim 16, wherein the catalyzed sensor element and the sensor element are located in an elevated gas temperature region and the signal conditioning circuitry is in a lower temperature region removed from the gas stream.

18. The gas sensor of claim 1, wherein the catalyzed sensor element and the sensor element are fifty degrees Celsius or less of each other during operation of the gas sensor.

19. A gas sensor for being placed into a gas stream that is insensitive to a rotational orientation positioning within the gas stream, comprising:
   a) a base having a longitudinal axis that is, during operation of the gas sensor, oriented at an angle to the gas stream flowing there over; and
   b) a sensor element and a catalyzed sensor element, wherein:
      b1) the sensor element is proximate to the catalyzed sensor element on the base with a sufficient separation therebetween along the axis of the base to ensure that the gas stream has no substantial flow path portion that flows over both the sensor element and the catalyzed sensor element, and
      b2) the sensor element and the catalyzed sensor element are further positioned so that the base could be rotationally orientated anywhere about the longitudinal axis and not have a same portion of the gas stream flowing over the catalyzed sensor element and then over the sensor element.

20. The gas sensor of claim 19, wherein the catalyzed sensor element and the sensor element are fifty degrees Celsius or less of each other during operation of the gas sensor.

21. The gas sensor of claim 20, wherein both the sensor element and the catalyzed sensor element are arcuate in shape.

22. The gas sensor of claim 19, wherein
   the a sensor element is positioned on the base, for sensing a first temperature at a first point along the gas stream; and
   the catalyzed sensor element, is designed for creating an exothermic reaction upon contacting the gas stream thereby forming a heated gas stream portion having a second temperature equal to or hotter than the first temperature, and the catalyzed sensor element if positioned on the base so that the heated gas stream portion does not contact the sensor element.

23. The gas sensor of claim 20, wherein
   the a sensor element is positioned on the base, for sensing a first temperature at a first point along the gas stream; and
   the catalyzed sensor element, is designed for creating an exothermic reaction upon contacting the gas stream thereby forming a heated gas stream portion having a second temperature equal to or hotter than the first temperature, and the catalyzed sensor element if positioned on the base so that the heated gas stream portion does not contact the sensor element.

24. A gas sensor that is insensitive to any rotational positioning within a gas stream while performing at least one measurement thereon, comprising:

a) a base having a longitudinal axis that is oriented at an angle to the gas stream;

b) a first and second sensor element fixed on the base with sufficient separation therebetween along the axis so no substantial gas stream portion flows over both the first and second sensor elements when the base is rotationally oriented to assume any rotational position about the axis c) the second sensor element is positioned on the base, for sensing a first temperature at a first point along the gas stream; and d) the first sensor element is a catalyzed sensor element, and is designed for creating an exothermic reaction upon contacting the gas stream thereby heating a portion of the gas stream to a second temperature that is equal to or hotter than the first temperature, and the first sensor element is positioned on the base for sensing the second temperature at a second point in the gas stream proximate to the first point and is further positioned so the portion of the gas stream at the second temperature will not contact the second sensor element.

25. The gas sensor of claim 24, wherein the catalyzed sensor element and the sensor element are fifty degrees Celsius or less of each other during operation of the gas sensor.

26. The gas sensor of claim 24, wherein the base has the axis orientated longitudinally, and during operation of the gas sensor, the axis is oriented at an angle to the gas stream flowing there over.

27. The gas sensor of claim 25, wherein the sensor element is proximate to the catalyzed sensor element on the base with a sufficient separation therebetween along the axis of the base to ensure that the gas stream has no substantial flow path portion that flows over both the sensor element and the catalyzed sensor element.

* * * * *